United States Patent [19]

Wu

[11] Patent Number: 5,779,708
[45] Date of Patent: Jul. 14, 1998

[54] INTRAOSSEOUS DRUG DELIVERY DEVICE AND METHOD

[75] Inventor: Gin Wu, Corte Madera, Calif.

[73] Assignee: Cyberdent, Inc., Novato, Calif.

[21] Appl. No.: 698,016

[22] Filed: Aug. 15, 1996

[51] Int. Cl.$^6$ ............................................. A61B 17/00
[52] U.S. Cl. .............................................. 606/80; 604/164
[58] Field of Search ............................ 606/80; 604/158, 604/161, 164, 165, 166; 433/165, 134

[56] References Cited

U.S. PATENT DOCUMENTS

| | | | |
|---|---|---|---|
| Re. 27,923 | 2/1974 | Bentov | 604/164 |
| 2,442,033 | 5/1948 | Brantly et al. | 32/28 |
| 3,406,685 | 10/1968 | May | 604/164 |
| 3,750,667 | 8/1973 | Pshenichny et al. | 604/164 |
| 4,021,920 | 5/1977 | Kirschner et al. | 433/82 |
| 4,193,197 | 3/1980 | Kuria et al. | 433/82 |
| 4,220,446 | 9/1980 | Walker | 433/87 |
| 4,787,893 | 11/1988 | Villette | 604/188 |
| 4,944,677 | 7/1990 | Alexandre | 433/92 VD |
| 4,973,247 | 11/1990 | Varnes et al. | 433/82 |
| 5,085,631 | 2/1992 | Leighton | 604/164 |
| 5,201,656 | 4/1993 | Sicurelli, Jr. | 433/166 |
| 5,275,568 | 1/1994 | Cohen et al. | 433/224 |
| 5,429,504 | 7/1995 | Peltier et al. | 433/165 |
| 5,554,154 | 9/1996 | Rosenburg | 606/80 |

FOREIGN PATENT DOCUMENTS

1430092  3/1976  United Kingdom ............... 604/158

OTHER PUBLICATIONS

Pearce, Jr. "Intraosseous Injection For Profound Anesthesia Of The Lower Molar" (1 page).
Cannell, et al. "Intraosseous Injections Of Lignocaine Local Anaesthetics" *British Dental Journal*, vol. 141; Jul. 20, 1976; pp. 48–50.

Lilienthal "A Clinical Appraisal Of Intraosseous Dental Anesthesia", Oral Surg., vol. 39, No. 5; May 1975; pp. 692–697.

Bourke "Intra–Osseous Anaesthesia" *Dent. Anaesthesia And Sedation*, vol. 3, No. 2, Jul. 1974, pp. 13–18.

Dorfman "Predictable And Effective Anesthesia Utilizing Intraosseous Injections".

Leonard "The Efficacy Of An Intraosseous Injection System of Delivering Local Anesthetic".

Magnes "Intraosseous Anesthesia", Anesthesia Progress, Nov. 1968, pp. 264–267.

Garfunkel, et al. "Intraligamentry—Intraosseous Anesthesia", Int. J. Oral Surg. 1983; 12: 334–339.

Biddulph "Intraosseous Anesthesia For Dental Procedures", The Arizona Dental Journal.

*Primary Examiner*—Michael Buiz
*Assistant Examiner*—Julian W. Woo
*Attorney, Agent, or Firm*—Limbach & Limbach, LLP

[57] ABSTRACT

An intraosseous and/or hard tissue drug delivery device and method is disclosed that perforates hard tissue and provides a drug delivery passage into underlying tissue. The device of the present invention includes a hollow drill bit and a stylet removably inserted into the hollow drill bit. The stylet keeps the bore of the hollow drill bit from plugging up during drilling. The stylet is removed after drilling to permit the operator to inject medication through the bore of the hollow drill bit.

17 Claims, 6 Drawing Sheets

INTRAOSSEOUS DRUG DELIVERY DEVICE AND METHOD

FIELD OF THE INVENTION

This invention relates to medical devices used to deliver medication through or into bone and other hard tissue. In particular, this invention relates to a medication injection device with a hollow drill bit useful for delivering medication through the hollow drill bit. The invention also relates to a method of using the medication injection device for intraosseous drug delivery.

BACKGROUND OF THE INVENTION

Dentists often administer local anesthetic to patients to minimize pain during dental procedures. Many dentists and patients, however, are dissatisfied with the results that dentists achieve using traditional anesthetic injection techniques. Problems with administration of anesthetic include: delays between injection and effect, the long duration and extent of postoperative numbness for patients, and the occasional inability to achieve total anesthesia.

One prior art solution was an intraosseous injection technique developed in the early 1900's. This intraosseous injection technique involved a three-step procedure. First, the gingiva over a target point of perforation (the point between the problem tooth and the adjacent tooth) was topically anesthetized. Second, a dentist drilled through the cortical plate of the jaw bone to create a hole. Lastly, a solution of local anesthetic was injected through the hole into the cancellous bone. The intraosseous injection technique eliminated some of the problems of the traditional injection. The anesthetic took effect quickly and effectively and caused little postoperative numbness. In addition, unlike other techniques, it worked well in almost all patients. However, the intraosseous injection technique had many problems. In addition to being difficult to perform, the technique produced large holes causing significant bone trauma with increased risk of bone infection.

One prior improvement of the intraosseous injection technique was the development of the Stabident System which involved the use of a drill with a small diameter (0.016 inch) drill bit. The use of small drill bit reduced tissue damage and the risk of infection. In spite of these advantages, however, the Stabident System had several drawbacks. In particular, dentists were still required to switch to a hypodermic needle to inject anesthetic once a hole was drilled with the small drill bit. This injection step was difficult because the opening produced by the small drill bit was often difficult to locate because it is covered by soft tissue. Another problem with the Stabident system was that stainless still drill bits were not properly tempered, so that the drill bits occasionally wore out prematurely. Worn out drill bits generated excessive heat during use that caused heat damage to the surrounding bone tissue. In addition, excessive heat levels occasionally caused melt-down and detachment of a plastic hub attached to the drill bit, which resulted in the detached drill head being left inside the patient's jaw bone leading further complications.

Rotary dental tools with hollow bits have been used in the past as a grinding tool. Such a tool has a low speed and relatively large-diameter hollow bit for grinding bone while supplying water to the grinding area to lubricate and flush particles. However, this art does not disclose a means to supply anesthetic or medication to a tooth.

SUMMARY OF THE INVENTION

In order to meet these concerns, the present invention is directed to an intraosseous and/or hard tissue drug delivery device and method that provide a easily identified drug delivery passage for the operator, which thereby greatly extends the applicability of the intraosseous injection technique. In other words, this invention is an intraosseous and/or hard tissue drug delivery system that perforates the hard tissue and also provides a clear drug delivery passage through the soft tissue.

The device of the present invention includes a hollow drill bit and a stylet removably inserted into the hollow drill bit to keep the bore of the hollow drill bit unplugged during drilling. The stylet is removed after drilling to permit the operator to inject medication through the bore of the hollow drill bit. Preferably, the hollow drill bit of the present invention is a hypodermic needle having a sharpened point.

An important feature of the invention is that the stylet is removable from the hollow drill bit. After the drilling, the stylet is removed and the tip of an injection needle is inserted into the bore of the hollow drill bit to dispense the medication through the bore. Another feature of the invention is that both the drill bit and stylet are disposable.

An advantage of the present invention is that it provides a effective intraosseous drug delivery system that maximizes the applicability of intraosseous injection technique with minimum complications of the device for dental and other potential medical applications. This invention provides the solution to the problems of intraosseous injection heretofore encountered by dentists in dental anesthesia. This invention also provides broader applicability of the intraosseous injection technique in dental anesthesia and other medication.

A preferred embodiment of the invention is a medication injection device that includes two basic parts: a hollow drill bit and a stylet. The stylet fits into the hollow drill bits from the hub end and extends through the entire length of the drill bit. The stylet has a enlarged handle on the hub end that is grasped to remove the stylet. The stylet prevents the bore of the hollow drill bit from plugging up during the drilling operation so that medication can be injected through the bore into the surrounding tissue after the stylet is removed.

The hollow drill bit is preferably sized at 27 G (gauge), so it will produce only a very small hole in the bone. It causes no significant damage to the bone structure. The highly hardened drill bit with its sharp cutting angle provides a smooth drilling action, preventing the generation of excessive heat. The process of sharpening the needle tip makes the diameter of tip portion slightly larger than the tubing portion, so that the diameter of the hole produced by the hollow drill bit is slightly larger that the diameter of the drill bit. This prevents the drill from jamming into the bone.

The stylet prevents the bore of the hollow drill bit from being plugged during the drilling. It also prevents any contamination from the hub side. Removing the stylet after drilling provides an easily identified injection passage for the injection needle.

Before this invention, intraosseous injection techniques in dental anesthesia encountered major difficulties with both patients and dentists. During the early development stage of intraosseous injection, the drill bits would cause tremendous bone damage to the patient and create a greater chance of inflammation and infection. At a later stage, a special drill was developed, but it was difficult for dentists to find the drilled hole under the gum tissue. Further, the usefulness of the prior technique was generally limited to the front teeth, because the limited space and angle made the application to the back teeth much more difficult. The present invention has eliminated these problems. The applicable area can expands to the whole mouth, and the fine needle drill will not produce significant bone damage.

This invention is not limited to injecting local anesthetics in dental applications. The invention is broadly usable for injecting a wide range of medications, including antibiotics, and in other medical and veterinary applications.

The features and advantages described in the specification are not all inclusive, and particularly, many additional features and advantages will be apparent to one of ordinary skill in the art in view of the drawings, specification and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

DETAILED DESCRIPTION OF THE PREFERRED EMBODIMENTS

FIGS. 1 through 14 of the drawings depict various preferred embodiments of the present invention for purposes of illustration only. One skilled in the art will readily recognize from the following discussion that alternative embodiments of the structures and methods illustrated herein may be employed without departing from the principles of the invention described herein.

Figure 1:
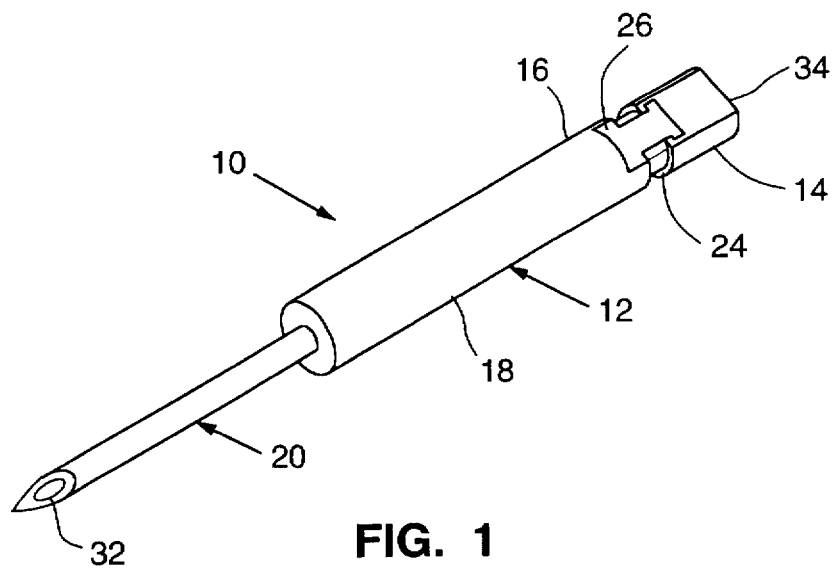
FIG. 1 is a prospective view of a medication injection device in an assembled state with a hollow drill bit and a stylet according to the present invention.
Figure 2A:
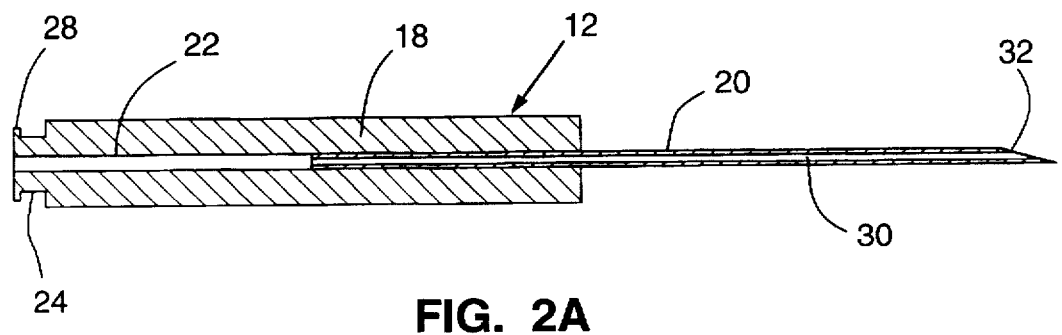
FIG. 2a is a longitudinal section of the hollow drill bit of FIG. 1 without the stylet.
Figure 2B:
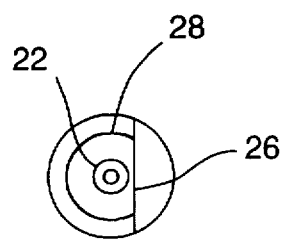
FIG. 2b is an end view from the hub end of the hollow drill bit of FIG. 1.

One aspect of the present invention is a medication injection device having a hollow drill bit and a stylet removably assembled in the bore of the hollow drill bit. The preferred embodiment of the medication injection device 10 is shown in FIG. 1. Medication injection device 10 includes a hollow drill bit 12 and a removable stylet 14. When assembled, the stylet 14 is positioned within a bore of the hollow drill bit 12 and has a small handle 34 extending rearwardly from the hub end 16 of the hollow drill bit.

The hollow drill bit 12 and the stylet 14 are shown in more detail in FIGS. 2–5. As shown in FIGS. 2a and 2b, the hollow drill bit 12 has a hollow cylindrical hub 18 and a needle 20 extending axially from one end of the cylindrical hub. The cylindrical hub 18 has an axial passage 22 therethrough and a circumferential groove 24 and a longitudinal flat 26 at the end opposite the needle 20. The dimensions of the hub 18 and its groove 24 and flat 26 are chosen so that the hollow drill bit 12 will mate with the spindle of a standard low-speed dental handpiece. The groove 24 on the end of the hub 18 is the retaining site for the latch on a standard low-speed dental handpiece. The end of the hub 18 opposite the needle also has a lip 28 that serves as an attachment structure for the stylet 14. The cylindrical hub 18 is preferably composed of stainless steel, aluminum or plastic.

The needle 20 is a preferably a 27 G (gauge) hypodermic needle, although larger or smaller sizes can also be used. The needle 20 is hollow with a bore 30 extending along its axis. The exposed end of the needle 20 is a sharpened tip 32.

Figure 3:
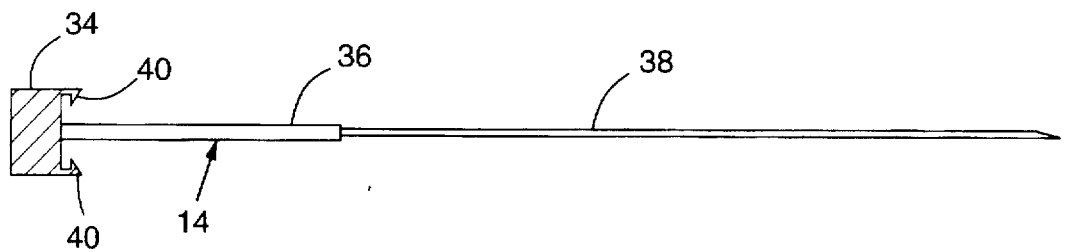
FIG. 3 is a longitudinal section of a snap-on stylet.

As the best shown in FIG. 3, the stylet 14 has a handle portion 34, a cylindrical body 36, and a wire 38. The handle 34 is cylindrical with a flat that corresponds to the flat 26 of the hollow drill bit 12. The handle 34 has a latch 40 that extends around and mates with the groove 26 and lip 28 of the hub 18 of the hollow drill bit 12. The handle 34 of the stylet is preferably made of plastic or stainless steel. The cylindrical body 36 of the stylet 14 is preferably made of stainless steel with a plastic coating, and has a diameter slightly smaller than the inside diameter of the axial passage 22 of the hub. The wire 38 of the stylet 14 is a straight stainless steel wire that precisely fits into the bore 30 of the hypodermic needle 20 of the hollow drill bit 12.

Figure 4:
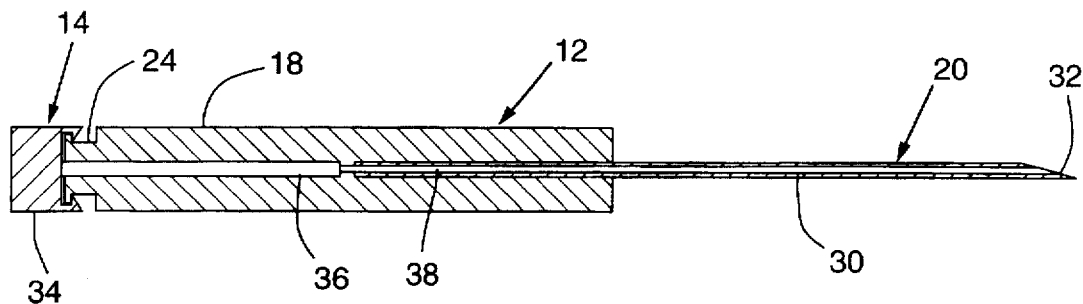
FIG. 4 is a longitudinal section of the medication injection device assembled with the snap-on stylet.
Figure 5:
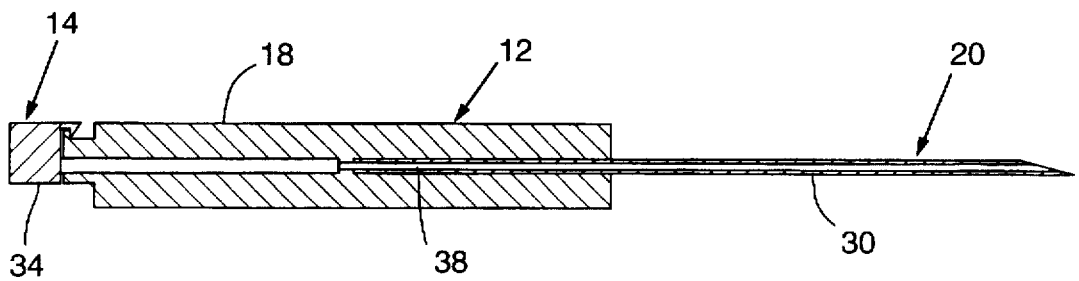
FIG. 5 is another longitudinal sections of the medication injection device assembled with the snap-on stylet, and is oriented at 90 degrees to the longitudinal section of FIG. 4.
Figure 6:
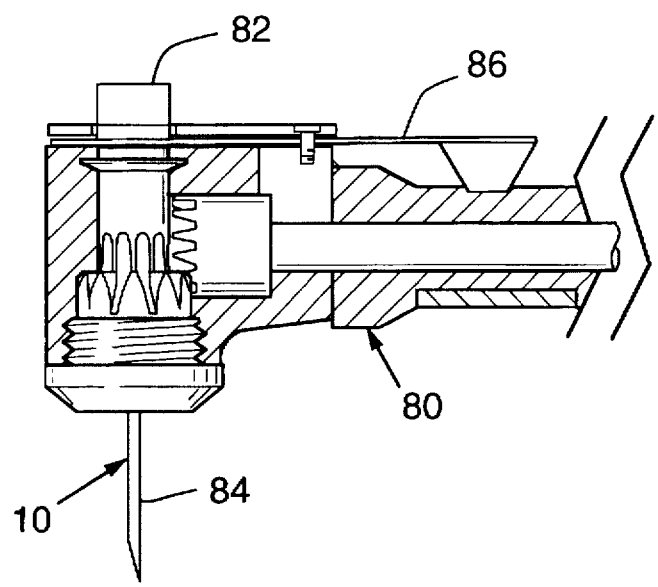
FIG. 6 is a view, partially in section, of the medication injection device installed in a drill head of a dental handpiece.
Figure 7:
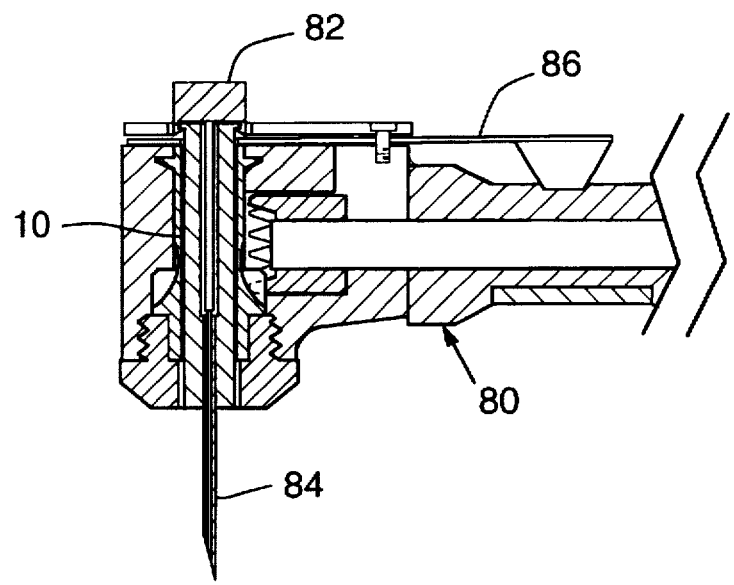
FIG. 7 is a sectional view of the medication injection device and drill head of FIG. 6.
Figure 8:
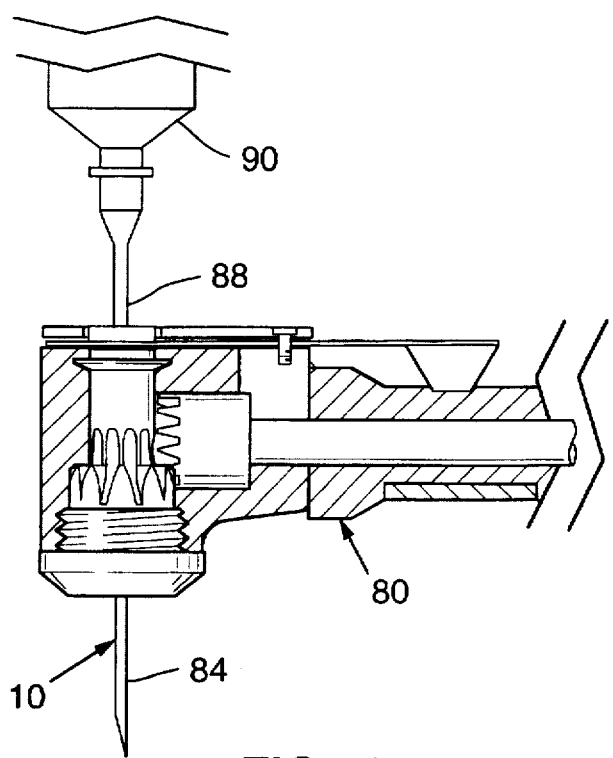
FIG. 8 is a view, partially in section, of the medication injection device installed in the drill head of that dental handpiece and with the stylet removed and a hypodermic needle inserted inside the bore of the hollow drill bit.
Figure 9:
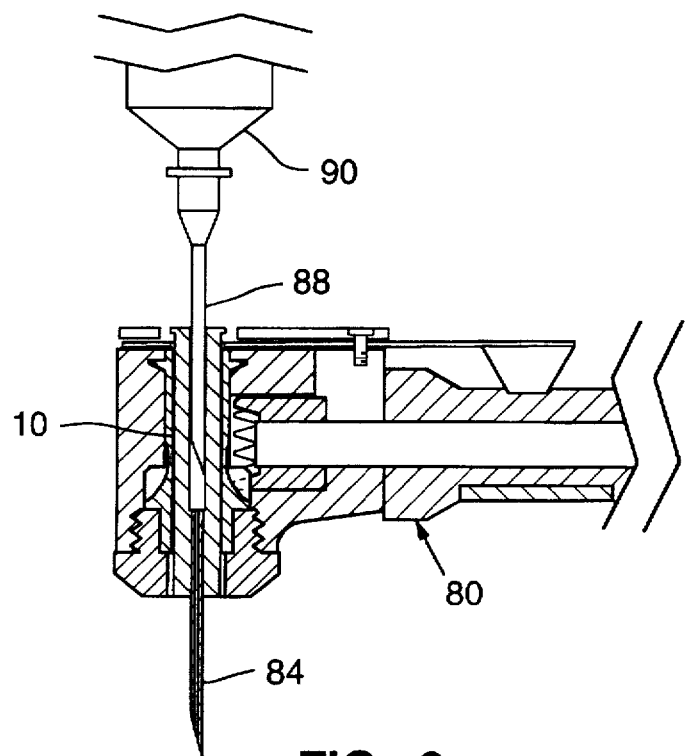
FIG. 9 is a sectional view of FIG. 8.
Figure 10:
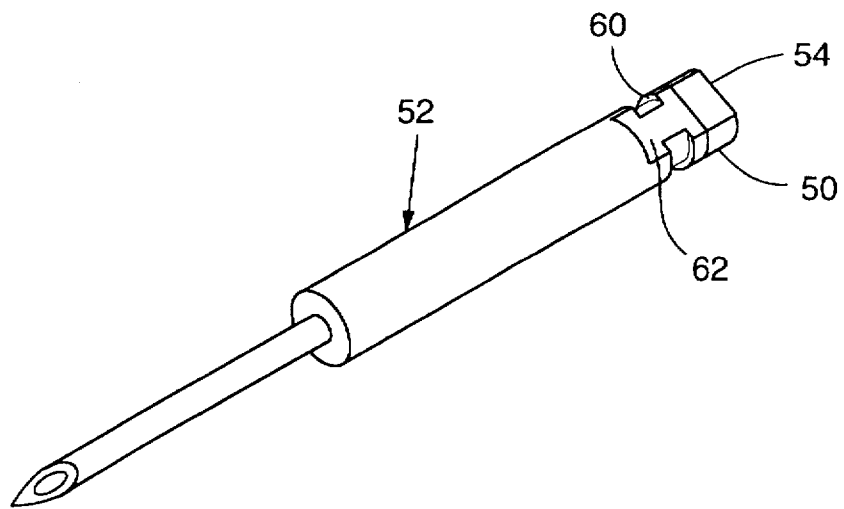
FIG. 10 is a prospective view of another embodiment of the medication injection device of the present invention, which has a tight-fit stylet.
Figure 11A:
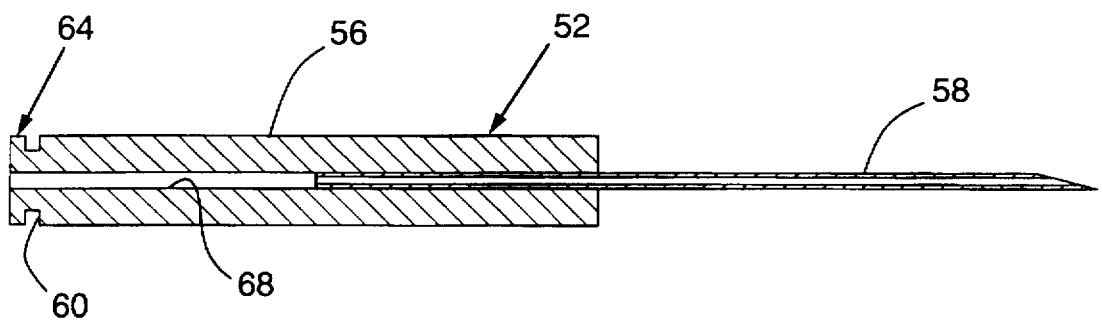
FIG. 11a is a longitudinal section of the hollow drill bit of FIG. 10 without the stylet.
Figure 11B:
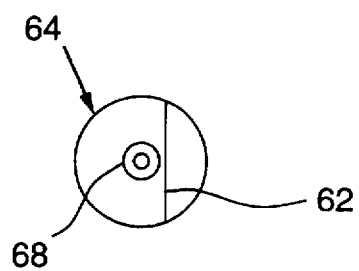
FIG. 11b is an end view from the hub end of the hollow drill bit of FIG. 10.
Figure 12:
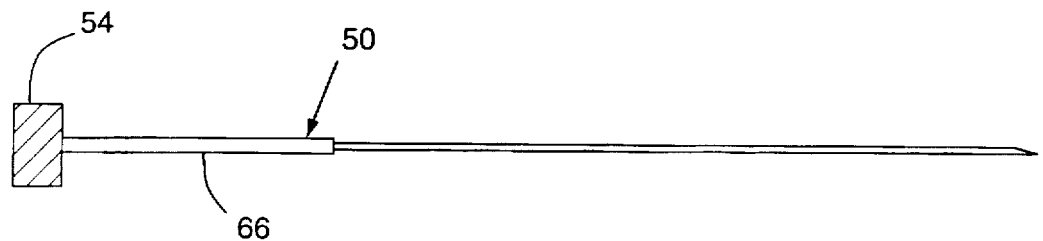
FIG. 12 is a longitudinal section of a tight-fit stylet.
Figure 13:
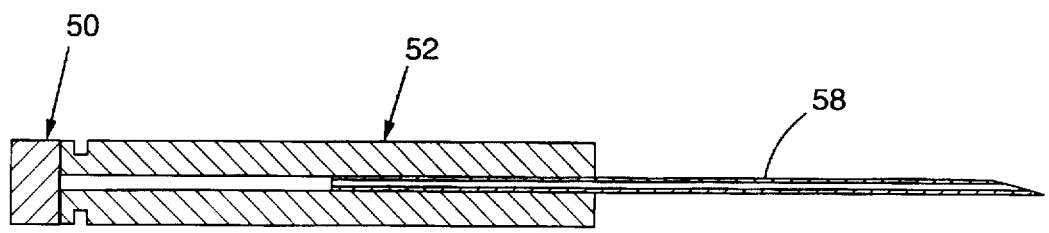
FIG. 13 is a longitudinal section of the medication injection device assembled with the tight-fit stylet.
Figure 14:
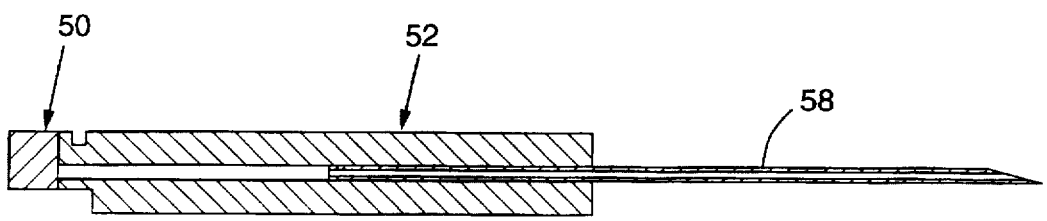
FIG. 14 is another longitudinal sections of the medication injection device assembled with the tight-fit stylet, and is oriented at 90 degrees to the longitudinal section of FIG. 13.

As shown in FIGS. 4 and 5, the stylet 14 is mounted into the hollow drill bit 12 with the wire portion 38 of the stylet passing through the entire length of the bore 30 of the hollow drill bit to the sharpened tip 32 of the hypodermic needle. The handle 34 of the stylet latches onto the end of the hub 18 to secure the stylet to the hollow drill bit.

In an alternative embodiment, shown in FIG. 10–14, a stylet 50 is designed for a tight, friction fit to the bore of a hollow drill bit 52. The handle 54 of the stylet has a cylindrical shape with a flat, but without a latch like the latch 40 of stylet 14. The end of the hub 56 of the hollow drill bit 52 opposite the needle 58 has a groove 60 and flat 62, and has a lip 64 that extends to the radius of the hub. The stylet 50 is secured by the tight fit of the middle portion 66 of the stylet to the bore 68 of the hub of the hollow drill bit 52.

A method of using the medication injection device 10 according to the present invention will now be described with reference to FIGS. 6–9. The hollow drill bit and the stylet are pre-assembled and sterilized and are installed into the spindle of a standard low-speed dental handpiece 80. The handle 82 of the stylet extends out the backside of the handpiece 80, and the needle 84 extends out the front side. A retainer 86 of the handpiece 80 latches onto the retains the hollow drill bit.

Once the medication injection device 10 is installed in the handpiece, the device is ready for use. The tip of the needle is positioned at the desired location and the handpiece is activated to drill into the subject. When the drilling is completed, the handpiece is stopped and the stylet is removed by grasping on the handle 82 and pulling the stylet out the backside. Removing the stylet opens the bore of the hollow drill bit for introduction of medication to the tip of the needle 84. After a hole has been drilled and the stylet removed, the operator inserts the hypodermic needle tip 88 of a syringe 90 containing the medication into the bore of the hub. The operator holds the handpiece to steady the hollow drill bit 10 during the injection phase. When the injection is complete, the operator withdraws the hollow drill bit 10 from the drilled hole by moving the handpiece 80.

Since the hollow drill design of the present invention provides a drug delivery passage passing through the covering soft tissue, the invention has many advantages over other existing devices. In comparison to the rosehead bur or reamer, this device will only drill a hole similar to the tiny diameter of a ordinary 27 G needle. Therefore, bone and tissue damage are significantly reduced. In comparison to the perforator used in Stabident System, the present invention provides a visible drug delivery passage on the surface of the soft tissue. Therefore, there is no more guessing and trial and error to find a tiny hole into the bone covered by soft tissue. Also, if it is necessary, operator may temporarily leave the hollow drill bit in position by removing the dental handpiece after releasing the retainer. This will allow the operator has the chance to dispense the second or more dosages to the same position.

The application field includes, but is not necessarily limited to, dental, medical and veterinary medicine. In order to avoid contamination among patients, the drill bit and the stylet are disposable.

While the invention has been disclosed with reference to drilling holes between teeth for applying a dental anesthetic, those skilled in the art will recognize that the invention will be useful for any procedure requiring the drilling of an opening and the delivery of fluid into tissue. From the above description, it will be apparent that the invention disclosed herein provides a novel and advantageous medication injection device and associated method of use. The foregoing discussion discloses and describes merely exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

What is claimed is:

1. A rotatable drilling device for use in injecting medication, said rotatable drilling device comprising:
   a rotatable hollow drill bit adapted for mounting in a spindle of a drill, wherein the rotatable hollow drill bit includes a hub and a needle extending outwardly from an end of the hub, wherein the needle has a sharpened tip, wherein the rotatable hollow drill bit has a bore extending through the hub and needle, and wherein an end of the hub opposite the needle has an opening through which medication can be introduced into the bore, wherein the hub further includes an adapter means for coupling the hub to the spindle for rotation therewith; and
   a stylet removably inserted in the bore of the rotatable hollow drill bit, wherein the stylet extends through the bore of the rotatable hollow drill bit to the tip of the needle.

2. A rotatable drilling device as recited in claim 1 wherein the hub is substantially cylindrical in shape and has a central axis, and wherein the bore is located along the central axis.

3. A rotatable drilling device as recited in claim 1 wherein the needle is a hypodermic needle having a sharpened point.

4. A rotatable drilling device as recited in claim 1 wherein the stylet has a handle that extends outwardly from the end of the hub opposite the needle.

5. A rotatable drilling device as recited in claim 1 wherein the stylet includes a latch, and wherein the end of the hub opposite the needle includes a groove that receives the latch when the stylet is inserted in the bore of the rotatable hollow drill bit.

6. A rotatable drilling device as recited in claim 1 wherein the stylet includes a cylindrical body that fits within the portion of the bore that is located in the hub of the rotatable hollow drill bit, and wherein the stylet further includes a cylindrical wire extending from the cylindrical body that fits within the portion of the bore that is located in the needle of the rotatable hollow drill bit.

7. A rotatable drilling device as recited in claim 6 wherein the cylindrical body of the stylet is a friction fit within the bore of the hub.

8. A rotatable drilling device as recited in claim 1, wherein the adapter means includes a longitudinal flat on the hub.

9. A rotatable drilling device for use in injecting medication, said rotatable drilling device comprising:
   a rotatable hollow drill bit having an axis of rotation and being adapted for mounting in a spindle of a drill;
   the rotatable hollow drill bit including a hub having a bore extending therethrough along the axis of the hollow drill bit, wherein the hub has an opening in one end thereof through which medication can be introduced into the bore, and wherein the hub further includes an adapter means for coupling the hub to the spindle for rotation therewith;
   the rotatable hollow drill bit including a hypodermic needle extending outwardly from an end of the hub opposite said opening and along the axis of the rotatable hollow drill bit, wherein the hypodermic needle has a sharpened tip;
   a stylet removably inserted in the bore of the hub, wherein the stylet has a handle at one end that extends outwardly from said opening in the hub, and wherein the stylet has a wire at an opposite end that extends through the interior of the needle to the tip of the needle.

10. A medication injection device comprising:
    a rotatable hollow drill bit adapted for mounting in a spindle of a drill, wherein the rotatable hollow drill bit includes a hub and a first needle extending outwardly from one end of the hub, wherein a distal end of the first needle has a sharpened tip, wherein the rotatable hollow drill bit has a bore extending through the hub and first needle;
    a stylet removably received in the bore of the rotatable hollow drill bit, wherein the stylet extends through the bore to the tip of the first needle, and wherein the hub further includes an adapter means for coupling the hub to the spindle for rotation therewith;
    a syringe having a second needle adapted for insertion into the bore of the rotatable hollow drill bit when the stylet is removed from the rotatable hollow drill bit.

11. A medication injection device as recited in claim 10 wherein the hub is substantially cylindrical in shape and has a central axis, and wherein the bore is located along the central axis.

12. A medication injection device as recited in claim 10 wherein the first needle is a hypodermic needle having a sharpened point.

13. A medication injection device as recited in claim 10 wherein the stylet has a handle that extends outwardly from the end of the hub opposite the needle.

14. A medication injection device as recited in claim 10 wherein the stylet includes a latch, and wherein the end of the hub opposite the needle includes a groove that receives the latch when the stylet is received in the bore of the rotatable hollow drill bit.

15. A medication injection device as recited in claim 10 wherein the stylet includes a cylindrical body that fits within the portion of the bore that is located in the hub of the rotatable hollow drill bit, and wherein the stylet further includes a cylindrical wire that extends from the cylindrical body and that fits within the portion of the bore that is located in the needle of the rotatable hollow drill bit.

16. A medication injection device as recited in claim 15 wherein the cylindrical body of the stylet is a friction fit within the bore of the hub.

17. A rotatable drilling device as recited in claim 10, wherein the adapter means includes a longitudinal flat on the hub.

* * * * *